United States Patent [19]

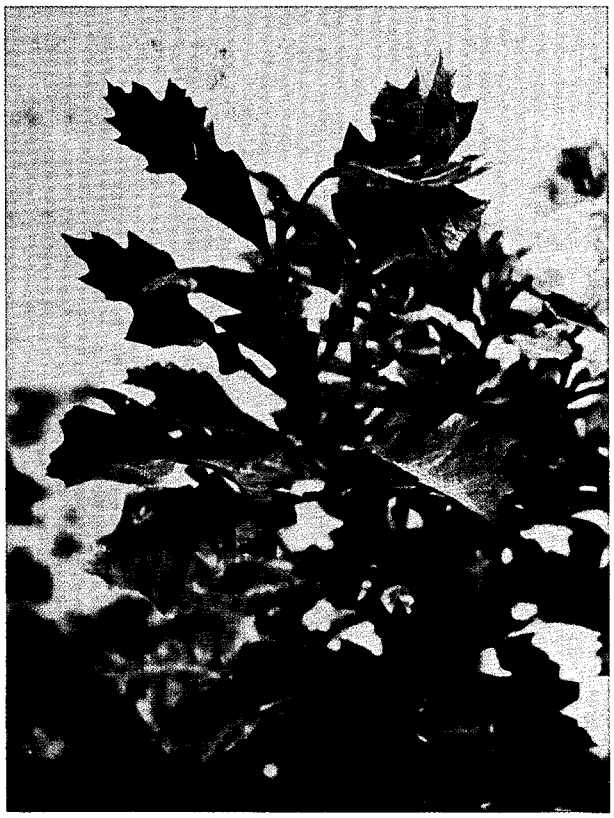
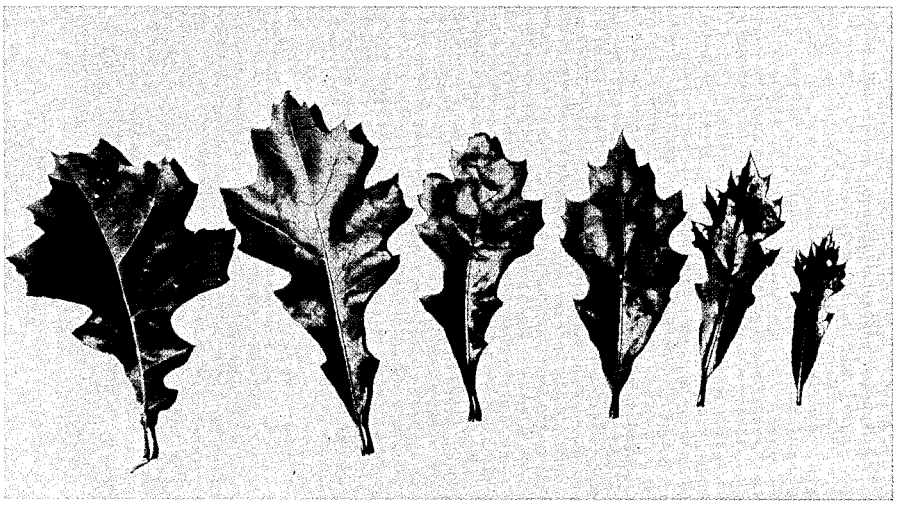

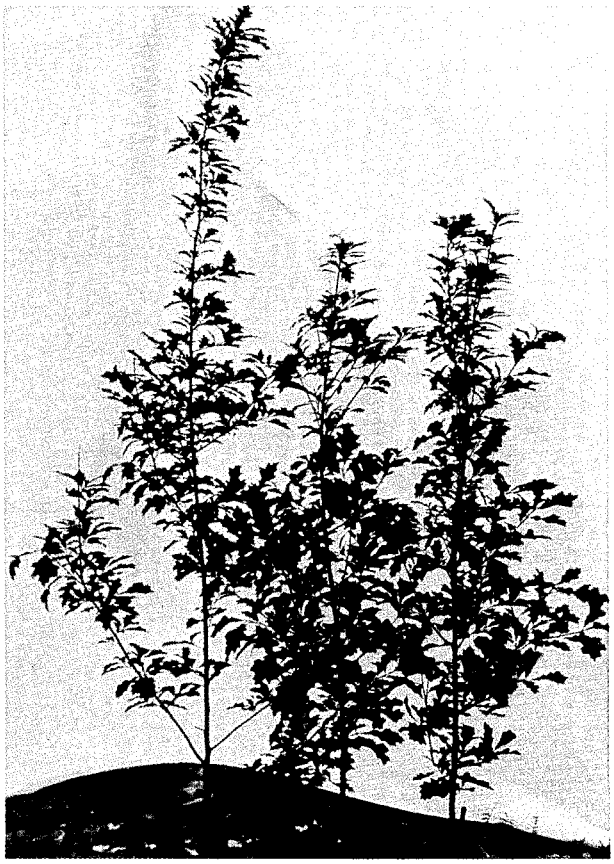
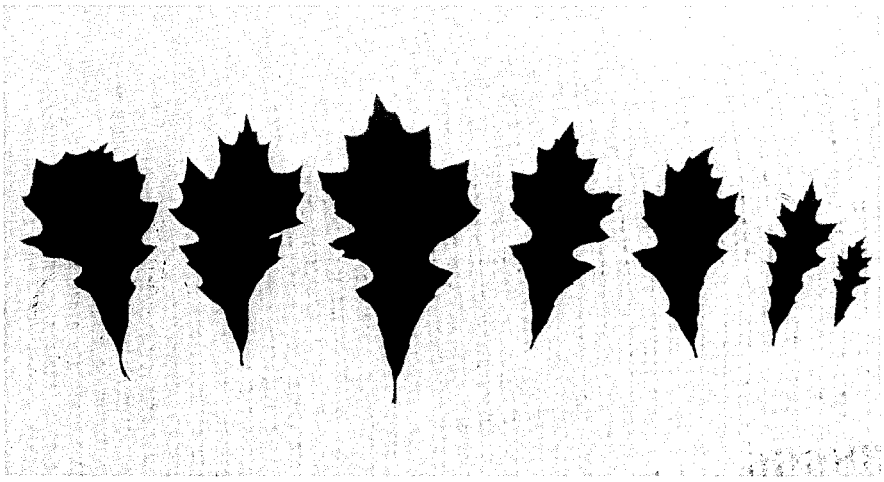

Schmidt, III

[11] Plant 4,149

[45] Nov. 15, 1977

[54] OAK TREE

[76] Inventor: J. Frank Schmidt, III, 19237 NE. Halsey St., Portland, Oreg. 97230

[21] Appl. No.: 738,666

[22] Filed: Nov. 4, 1976

[51] Int. Cl.[2] ..... A01H 5/12

[52] U.S. Cl. ..... Plt./51

[58] Field of Search ..... Plt./51

*Primary Examiner*—Robert E. Bagwill

*Attorney, Agent, or Firm*—Klarquist, Sparkman, Campbell, Leigh, Hall and Whinston

[57] ABSTRACT

This invention relates to a novel variety of Shumard Oak, distinguished by its immature leaf color which is maroon until late spring or early summer, then turning into green.

2 Drawing Figures

1

The present invention relates to a new and distinct variety of oak tree of the species botanically known as *Quercus shumardii* and commonly called "Shumard oak." I discovered my new variety as a seedling mutation of unknown parentage among a group of nursery plants of the Shumard oak variety which were being grown in a cultivated area of a nursery in Boring, Oreg.

While engaged in the routine care of the nursery, my attention was first attracted to the new seedling among a row of Shumard oak seedlings because of the coloration of its leaves. At that time, the leaves of the new seedling were a deep maroon, while the leaves of the other Shumard oak seedlings in the nursery were green. Close observations of the new seedling and continued observations of progeny thereof subsequently asexually propagated by me in Boring, Oreg. by budding, confirmed that the unique leaf coloration of the new variety was the result of a seedling variation. I am, therefore, convinced that my new tree represents a new and improved variety of *Quercus shumardii,* as particularly evidenced by the following unique combination of characteristics which have proven firmly fixed, are outstanding therein, and which distinguish it from all other varieties of this species:

1. Leaves which when newly formed are deep maroon in color; and

2. The long-lastingness of the maroon coloration of such leaves which gives the entire tree a distinct and highly ornamental maroon appearance until late spring or early summer.

The accompanying photographs depict a color of the foliage of my new variety as nearly true as is reasonably possible to make the same in a color illustration of this character.

FIG. 1 is a color photograph of a branch of a tree of the present invention taken on June 29, 1977 to show the maroon appearance of the leaves of the tree, FIG. 2 is a color photograph of leaves of the tree of my invention taken at the same time as the photograph of FIG. 1.

As previously indicated, the newly formed leaves are maroon. Thereafter, as the leaves age, they gradually turn to an olive green color. FIG. 2 depicts this progressive change in color from the young leaf on the right to the more mature leaf on the left. In addition, the maroon new growth leaves which appear late in the growing season contrast with those leaves which have turned green to give the tree an attractive multicolor look.

2

The leaves of other Shumard oak trees, unlike my new variety, are green in the spring. In fact, in mid-June 1976, the Shumard oak trees, except for my new variety, growing in the area where my nursery aforesaid is located, all had green leaves, while at the same time, the entire tree of my new variety had a maroon appearance. Otherwise, my new variety generally is typical of the species.

The following is a detailed description of my new variety of *Quercus shumardii,* with color terminology in accordance with the "Royal Horticultural Society Color Chart" (hereinafter R.H.S.), published by the Royal Horticultural Society of London. It is pointed out, however, that the coloration of the leaves as indicated below is only approximate because the coloring varies considerably as the leaves age. In addition, the size and shape of the leaves varies from tree to tree and depend upon the nature of the growing season.

Parentage: A seedling mutation of unknown parentage.

Propagation: Holds to distinguishing characteristics through succeeding propagation by budding.

Locality where grown and observed: Boring, Oreg.

Tree: Upright, healthy.

Foliage:

*Shape.*—Obovate to oval.

*Size.*—Typically 3 to 5 inches long and 2 to 4 inches broad.

*Apex.*—Acuminate to acute.

*Base.*—Cuneate.

*Margin.*—Typically seven to nine lobes, with many bristle tips. The lobes are often subdivided into secondary lobes by sinuses.

*Color.*—As described above and more specifically: Initially the leaf is a deep maroon color (similar to RHS 187A) which gradually changes with age to a lighter maroon color (somewhat darker than RHS 183A) and then to an olive green with a maroon cast (not shown in RHS). Eventually, the leaf turns to an olive green to green color (generally like RHS 137C) similar to the color of the leaf of other Shumard oaks.

I claim:

1. A new and distinct variety of oak tree substantially as herein shown and described, characterized particularly as to novelty by the maroon coloration of its newly formed leaves which coloration is long-lasting to give the entire tree a distinct maroon appearance until late spring or early summer.

* * * * *

UNITED STATES PATENT AND TRADEMARK OFFICE

CERTIFICATE OF CORRECTION

PATENT NO. : Plant 4,149

DATED : November 15, 1977

INVENTOR(S) : OAK TREE

It is certified that error appears in the above-identified patent and that said Letters Patent are hereby corrected as shown below:

In the drawing: Sheet 2 of 2 should be deleted in its entirety.

Sheet 1 of 2; amend to label the upper figure on this sheet as --Fig. 1-- and to label the lower figure on this sheet as --Fig. 2--.

Sheet 1 of 2; change the sheet number from "Sheet 1 of 2" to --Sheet 1 of 1--.

Signed and Sealed this

*Sixteenth* Day of *May 1978*

[SEAL]

*Attest:*

RUTH C. MASON
*Attesting Officer*

LUTRELLE F. PARKER
*Acting Commissioner of Patents and Trademarks*